United States Patent [19]

Hofer et al.

[11] 4,057,418
[45] Nov. 8, 1977

[54] SULFONYLMETHYLAMINO-SUBSTITUTED BENZOIC ACIDS AND HERBICIDAL METHOD THEREWITH

[75] Inventors: Wolfgang Hofer; Fritz Maurer; Hans-Jochem Riebel; Rolf Schröder, all of Wuppertal; Ludwig Eue, Cologne, all of Germany

[73] Assignee: Bayer Aktiengesellschaft, Leverkusen, Germany

[21] Appl. No.: 650,580

[22] Filed: Jan. 19, 1976

[30] Foreign Application Priority Data

Feb. 3, 1975 Germany ............................ 2504383

[51] Int. Cl.$^2$ ...................... A01N 9/14; C07C 147/11; C07C 147/107
[52] U.S. Cl. .................................. 71/103; 260/518 R; 260/518 A; 260/519; 260/558 S; 260/559 T; 560/12
[58] Field of Search ............... 260/518 R, 518 A, 519; 71/103

[56] References Cited

U.S. PATENT DOCUMENTS

| | | | |
|---|---|---|---|
| 3,036,063 | 5/1962 | De Le Mater et al. | 260/518 A |
| 3,629,320 | 12/1971 | Wasley | 260/518 A |
| 3,706,790 | 12/1972 | Sprague et al. | 260/518 R |
| 3,773,712 | 11/1973 | Borne | 260/518 A |
| 3,843,662 | 10/1974 | Holland | 260/518 A |
| 3,991,097 | 11/1976 | Bormann et al. | 260/518 A |

*Primary Examiner*—Norman Morganstern
*Attorney, Agent, or Firm*—Burgess, Dinklage & Sprung

[57] ABSTRACT

Novel benzoic acid compounds of the formula

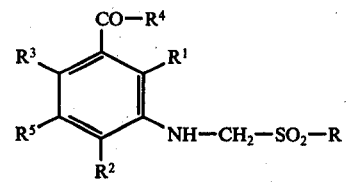

in which
R is alkyl or substituted alkyl of up to 6 carbon atoms, where the substituents are selected from halogen, or
R is aryl which is optionally substituted by halogen and/or by alkyl of up to 4 carbon atoms,
$R^1$ is alkyl, alkoxy or alkylmercapto, of in each case up to 4 carbon atoms, or halogen,
$R^2$ is hydrogen,
$R^3$ is hydrogen or halogen,
$R^4$ is hydroxyl, alkoxy of 1 to 6 carbon atoms or an amino group which is optionally substituted by one or two alkyl radicals each of up to 6 carbon atoms, and
$R^5$ is halogen or alkyl of up to 4 carbon atoms; are outstandingly effective and selective as herbicides.

10 Claims, No Drawings

SULFONYLMETHYLAMINO-SUBSTITUTED BENZOIC ACIDS AND HERBICIDAL METHOD THEREWITH

The present invention relates to new benzoic acid compounds, to herbicidal compositions containing them, and to their use as herbicides.

It is known that various substituted benzoic acids have herbicidal properties. Thus, for example, 2,5-dichloro-3-aminobenzoic acid can be employed to combat weeds as taught in German Auslegeschrift (German Published Specification) 1,115,516. However, the selective herbicidal activity of this compound is not always entirely satisfactory.

The present invention provides the benzoic acid derivatives of the general formula

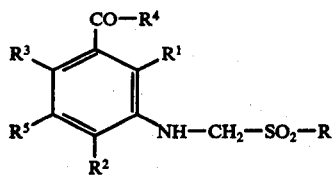

in which
R is alkyl or substituted alkyl of up to 6 carbon atoms, where the substituents are selected from halogen, or
R is aryl which is optionally substituted by halogen and/or by alkyl of up to 4 carbon atoms,
$R^1$ is alkyl, alkoxy or alkylmercapto, of in each case up to 4 carbon atoms, or halogen,
$R^2$ is hydrogen,
$R^3$ is hydrogen or halogen,
$R^4$ is hydroxyl, alkoxy of 1 to 6 carbon atoms or an amino group which is optionally substituted by one or two alkyl radicals each of up to 6 carbon atoms, and
$R^5$ is halogen or alkyl of up to 4 carbon atoms.

The compounds of the formula (I) have been found to possess outstanding herbicidal properties.

Preferably, R is alkyl of 1 to 4 carbon atoms, which is optionally substituted by chlorine, or is aryl of from 6 to 10 carbon atoms (especially phenyl) which is optionally substituted by alkyl of 1 to 4 carbon atoms and/or by chlorine and/or by bromine, $R^1$ is alkyl, or alkylmercapto, of in each case 1 or 2 carbon atoms, chlorine or bromine, $R^2$ is hydrogen, $R^3$ is hydrogen, chlorine or bromine, $R^4$ is hydroxyl, alkoxy of 1 to 4 carbon atoms or an amino group which is optionally substituted by one or two alkyl radicals each of 1 to 4 carbon atoms, and $R^5$ is chlorine, bromine or an alkyl radical of 1 to 2 carbon atoms.

Surprisingly, the benzoic acid derivatives according to the invention show as good as herbicidal activity as 2,5-dichlorine-3-amino-benzoic acid, known from the state of the art, which is chemically the nearest compound of the same type of action. In addition, the compounds according to the invention are more suitable for the selective combating of weeds than is the said compound of the prior art. The active compounds according to the invention thus represent a valuable enrichment of the art.

The present invention also provides a process for the preparation of a benzoic acid derivative of the general formula (I) in which a 3-aminobenzoic acid derivative of the general formula

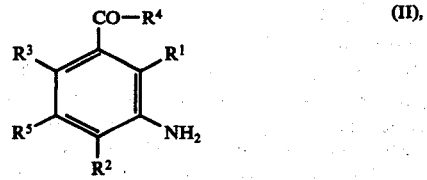

in which
$R^1$, $R^2$, $R^3$, $R^4$ and $R^5$ have the above-mentioned meanings, is reacted with a compound of the general formula $$HO\text{-}CH_2\text{-}SO_2\text{-}R \qquad (III)$$

in which R has the above-mentioned meaning, in the presence of an acid and, if appropriate, in the presence of a solvent or diluent.

If 2,5-dichloro-3-aminobenzoic acid and hydroxymethylphenylsulfone are used as starting materials, the course of the reaction can be represented by the following equation:

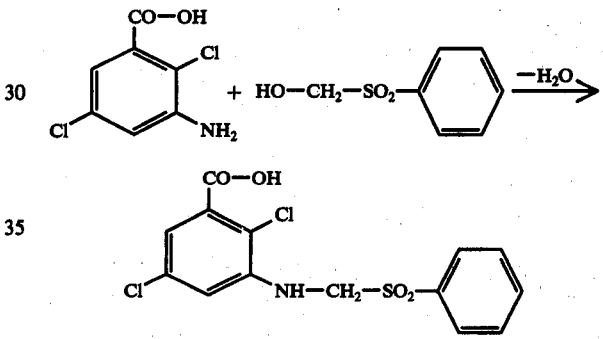

The 3-aminobenzoic acid derivatives of the formula (II) which can be used according to the invention are already known or can be prepared in accordance with generally customary processes (see R. Schroter and F. Moller in Houben-Weyl-Muller: "Methoden der organischen Chemie" ("Methods of Organic Chemistry"), volume 11/1, Thieme-Verlag Stuttgart (1957), pages 341–731).

The following may be mentioned as examples of the compounds of the formula (II): 2,5-dichloro-3-amino-, 2,5-dibromo-3-amino-, 3-amino-2,5-dimethyl-, 5-chloro-3-amino-2-methoxy-, 5-bromo-3-amino-2-methyl-, 5-chloro-3-amino-2-methyl-, 5-bromo-3-amino-2-methyl-, 5-bromo-3-amino-2-methyl-mercapto, 5-chloro-3-amino-2-methylmercapto-, 5-chloro-2-bromo-3-amino-, 2-chloro-5-bromo-3-amino-, 2-bromo-3-amino-5-methyl- and 2-chloro-3-amino-5-methyl-benzoic acid, the methyl, ethyl, propyl, isopropyl, butyl and sec.-butyl esters and the methylamide, ethylamide, propylamide, isopropylamide, butylamide, sec.-butylamide, isobutylamide, dimethylamide, methylethylamide, diethylamide, methylpropylamide and ethylpropylamide of these acids, and the derivatives substituted by chlorine in the 6-position.

The compounds of the formula (III) which can be used according to the invention are known or can be prepared in accordance with generally customary processes (see A. Schoberl and A. Wagner in Houben- Weyl-Muller: "Methoden der organischen Chemie" ("Methods of Organic Chemistry"), volume 9, Thieme-Verlag, Stuttgart (1955), pages 250–252).

The following may be mentioned as examples of the compounds of the formula (III): hydroxymethyl-methyl-sulfone, hydroxymethyl-ethyl-sulfone, hydroxymethyl-propyl-sulfone, hydroxymethyl-isopropyl-sulfone, hydroxymethyl-n-butyl-sulfone, hydroxymethyl-isobutyl-sulfone, hydroxymethyl-sec.-butyl-sulfone, hydroxymethyl-tert.-butyl-sulfone, hydroxymethyl-($\beta$-chloroethyl)-sulfone, hydroxymethyl-phenyl-sulfone, hydroxymethyl-(4-methylphenyl)-sulfone and hydroxymethyl-(4-chlorophenyl)-sulfone.

The process according to the invention for the preparation of the new benzoic acid derivatives of the formula (I) is preferably carried out in the presence of suitable solvents or diluents. As such, water or inert organic solvents can be used, especially aliphatic and aromatic hydrocarbons, such as petroleum ether, benzene, toluene and xylene; chlorinated aliphatic and aromatic hydrocarbons, for example methylene chloride, chloroform, carbon tetrachloride, ethylene chloride and chlorobenzene; ethers, such as diethyl ether, dibutyl ether, tetrahydrofuran and dioxan; ketones, such as acetone, methyl ethyl ketone, methyl isopropyl ketone and methyl isobutyl ketone; and nitriles, such as acetonitrile and propionitrile.

All customary mineral acids can be used as the acids in carrying out the process according to the invention. Sulfonic acid, hydrochloric acid and phosphoric acid may be 100° C, preferably between 20° and 50°

The reaction temperatures can be varied within a fairly wide range. In general, the reaction is carried out at between 0° C and 100° C, preferably between 20° and 50° C.

The reaction according to the invention is in general carried out under normal pressure.

In carrying out the process according to the invention for the preparation of the compounds of the formula (I), 1 to 1.5 moles, preferably 1.2 moles, of a compound of the formula (III) and 0.2 to 1.5 moles, preferably 1 mole, of acid are preferably employed per mole of a 3-amine-benzoic acid derivative of the formula (II).

In general, the reaction products of the formula (I) are isolated by filtering off the crystalline precipitate produced after completion of the reaction, drying it and subsequently recrystallizing it. The compounds of the formula (I) can be characterized by their melting point.

The following may be mentioned as examples of the benzoic acid derivatives according to the invention, of the formula (I): 2,5-dichloro-3-[($\beta$-chloroethyl)-sulfonylmethylamino]-benzoic acid, 2,5-dibromo-3-methylsulfonylmethylamino-benzoic acid, 2,5-dichloro-3-phenylsulfonylmethylamino-benzoic acid, 2,5-dichloro-3-[(4-chlorophenyl)-sulfonylmethylamino]-benzoic acid, 2,5-dichloro-3-[(4-methylphenyl)sulfonylmethylamino]-benzoic acid, 2,5-dichloro-3-methylsulfonylmethylamino-benzoic acid, 2,5-dichloro-3n-butyl-sulfonylmethylamino-benzoic acid, 2,5-dimethyl-3-phenylsulfonylmethylamino-benzoic acid methyl ester, 2,5,6-trichloro-3-[(4-chlorophenyl)sulfonylmethylamino]-benzoic acid, 2,5,6-trichloro-3-[(4-methylphenyl)-sulfonylmethylamino]-benzoic acid, 2,5,6-trichloro-3-phenylsulfonylmethylamino-benzoic acid, 2,5,6-trichloro-3-methylsulfonylmethylamino-benzoic acid, 2,5-dichloro-3-ethylsulfonylmethylamino-benzoic acid, 2,5-dichloro-3-(n-butyl-sulfonyl-methylamino)-benzoic acid ethyl ester, 2,5-dichloro-3-isopropyl-sulfonylmethylamino-benzoic acid, 5-bromo-2-methoxy-[($\beta$-chloroethyl)-sulfonylmethylamino]-benzoic acid, 5-bromo-2-methylthio-[($\beta$-chloroethyl)-sulfonylmethylamino]-benzoic acid, 2-chloro-5-bromo-3-[($\beta$-chloroethyl)-sulfonylmethylamino]-benzoic acid, 2,5-dichloro-3-[(4-chlorophenyl)-sulfonylmethylamino]-benzoic acid ethyl ester, 2,5-dichloro-3-[(4-chlorophenyl)-sulfonylmethylamino]-benzoic acid methylamide and 2,5-dichloro-3-[(4-chlorophenyl)-sulfonylmethylamino]-benzoic acid diethylamide.

The preparation of the examples of this invention is illustrated by the following preparative Examples.

EXAMPLE 1 — Preparation of 2,5-dichloro-3-[($\beta$-chloroethyl)-sulfonylmethylamino]-benzoic acid 20.6 g (0.1 mole) of 2,5-dichloro-3-aminobenzoic acid and 18.7 g (0.12 mole) of hydroxymethyl-($\beta$-chloroethyl)-sulfone were suspended in 100 ml of ethylene chloride, 1 ml of concentrated sulfuric acid was added thereto and the mixture was stirred for 3 hours at 40° C. The mixture was then cooled and the product which had crystallized out was filtered off and recrystallized from acetonitrile. This gave 30.8 g (89% of theory) of 2,5-dichloro-3-[($\beta$-chloroethyl)-sulfonylmethylamino]-benzoic acid in the form of colorless crystals of melting point 156° C (with decomposition).

The compounds listed in Table 1 below, in Examples 2–13, were prepared analogously:

Table 1

$$\text{(I)}$$

Formula (I): benzene ring with substituents CO—R⁴, R¹, R², R³, R⁵, and NH—CH₂—SO₂—R

| Example No. | R | R¹ | R² | R³ | R⁴ | R⁵ | Yield (in % of theory) | Melting point (in ° C) |
|---|---|---|---|---|---|---|---|---|
| 2 |  | Cl | H | H | OH | Cl | 47 | 152 – 154 (decomposition) |
| 3 | 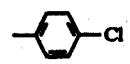 | Cl | H | H | OH | Cl | 56 | 154 (decomposition) |
| 4 | 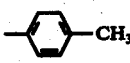 | Cl | H | H | OH | Cl | 16 | 148 (decomposition) |
| 5 | —CH₃ | Cl | H | H | OH | Cl | 32 | 168 (decomposition) |

Table 1-continued (I)

structure: benzene ring with CO—R⁴ at position, R³, R¹, R⁵, R², NH—CH₂—SO₂—R substituents

| Example No. | R | R¹ | R² | R³ | R⁴ | R⁵ | Yield (in % of theory) | Melting point (in °C) |
|---|---|---|---|---|---|---|---|---|
| 6 | —C₆H₄—Cl (4-chlorophenyl) | Cl | H | Cl | OH | Cl | 49 | 170 (decomposition) |
| 7 | —C₆H₄—CH₃ | Cl | H | Cl | OH | Cl | 61 | 182 |
| 8 | —C₆H₅ | Cl | H | Cl | OH | Cl | 49 | 162 (decomposition) |
| 9 | —CH₃ | Cl | H | Cl | OH | Cl | 50 | 176 |
| 10 | —C₂H₅ | Cl | H | H | OH | Cl | 22 | 172 |
| 11 | —C₄H₉-n | Cl | H | H | OH | Cl | 26 | 148 – 150 |
| 12 | —C₃H₇-iso | Cl | H | H | OH | Cl | 27 | 148 – 150 |
| 13 | —CH₂—CH₂—Cl | —OCH₃ | H | H | OH | Br | 39 | 120 (decomposition) |

EXAMPLE 14 — Preparation of 2-chloro-5-bromo-[(β-chloroethyl)sulfonylmethylamino]-benzoic acid

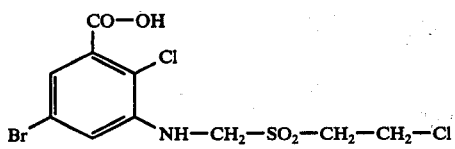

(14)

1 ml of concentrated sulfuric acid, followed by 9.6 g (60 mmoles) of hydroxymethyl-(β-chloroethyl)-sulfone were added at 60° C, whilst stirring, to a filtered solution of 12.6 g (50 moles) of 2-chloro-5-bromo-3-aminobenzoic acid in 150 ml of hot acetonitrile. The mixture was stirred for a further 2.5 hours at 50° C and was then cooled to 10° C, and the product which had precipitated was filtered off. It was rinsed with water and dried in air. 15 g (77% of theory) of 2-chloro-5-bromo-[(β-chloroethyl)-sulfonylmethylamino]-benzoic acid were obtained in the form of a yellow powder of melting point 164° C (with decomposition).

EXAMPLE 15 — Preparation of 2,5-dichloro-3-[(4-chlorophenyl)sulfonylmethylamino]-benzoic acid ethyl ester

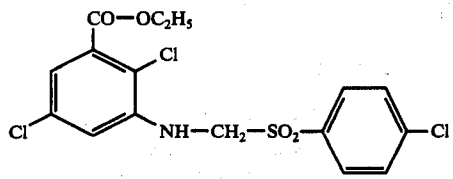

(15)

1 g of concentrated sulfuric acid was added to 2.32 g (10mmoles) of 2,5-dichloro-3-aminobenzoic acid ethyl ester, 2.27 g (11mmoles) of hydroxymethyl-(4-chlorophenyl)-sulfone and 40 ml of water whilst stirring at room temperature. The mixture was stirred for a further 3 hours at room temperature, the solid was filtered off and dissolved in about 100 ml of methylene chloride, the solution was dried over magnesium sulfate and worked up in the usual manner and the product was recrystallized from ethylene chloride. 3.0 g (71% of theory) of 2,5-dichloro-3-[(4-chlorophenyl)-sulfonylmethylamino]-benzoic acid ethyl ester were obtained in the form of colorless crystals of melting point 173°–175° C.

EXAMPLE 16 — Preparation of 2,5-dichloro-3-[(4-chlorophenyl)-sulfonylmethylamino]-benzoic acid N-methylamide

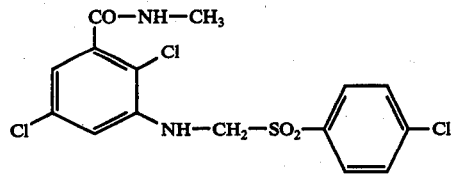

(16)

0.8 g of concentrated sulfuric acid was added to 1.8 g (8.2 mmoles) of 2,5-dichloro-3-aminobenzoic acid N-methylamide, 1.87 g (9 mmoles) of hydroxymethyl-(4-chlorophenyl)-sulfone and 50 ml of water whilst stirring at room temperature. The mixture was stirred for a further 2 hours at room temperature and the solid was then filtered off, washed with water and recrystallized from acetonitrile. 2.8 g (83% of theory) of 2,5-dichloro-3-[(4-chlorophenyl)-sulfonylmethylamino]-benzoic acid N-methylamide were obtained in the form of a colorless solid of melting point 175°–182° C (with decomposition).

The preparation of the starting compounds could be effected, for example, as follows:

EXAMPLE I — Preparation of 2,5-dichloro-3-amino-benzoic acid

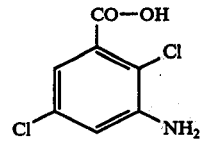

236 g (1 mole) of 2,4-dichloro-3-nitro-benzoic acid were dissolved in 1.5 l of ethanol and hydrogenated with Raney nickel as the catalyst at 20°–30° C. After the absorption of hydrogen had ceased, the catalyst was filtered off, the filtrate was evaporated and the residue was digested with benzene. 185 g (90% of theory) of 2,5-dichloro-3-amino-benzoic acid of melting point 197° C were obtained.

b. Preparation of 2,5-dichloro-3-nitro-benzoic acid 950 g (5 moles) of 2,5-dichloro-benzoic acid were suspended in 6 l of concentrated sulfuric acid. A mixture of 500 g of concentrated sulfuric acid and 400 g of nitric acid (D = 1.5) was added dropwise at 5° C to 10° C. The reaction mixture was stirred for 15 hours at 20°–25° C and was then poured onto 40 kg of ice. The precipitate which had separated out was filtered off, washed with 20 l of water and dried. The ultimate purification was carried out by recrystallization from 1.7 l of acetonitrile/water (9:1). 990 g (84% of theory) of 2,5-dichloro-3-nitrobenzoic acid were obtained in the form of colorless crystals of melting point 216°–218° C (with decomposition).

The compounds mentioned in Examples II-IV below were prepared analogously.

EXAMPLE II (a) 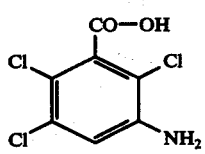  Yield = 64% of theory
Melting point >220° C (b) 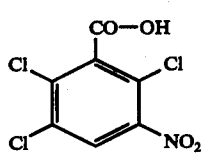  Yield = 74% of theory
Melting point 136–138° C

EXAMPLE III (a) 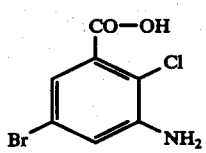  Yield = 68% of theory
Melting point 186–187° C (b) 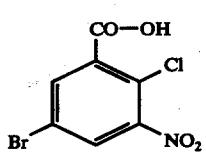  Yield = 72% of theory
Melting point 222–225° C

EXAMPLE IV (a) 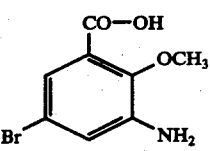  Yield = 40% of theory
Melting point 128–130° C (b) 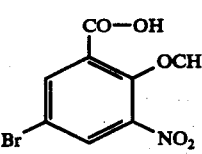  Yield = 96% of theory
Melting point 176° C

EXAMPLE V — Preparation of 2,5-dichloro-3-amino-benzoic acid ethyl ester

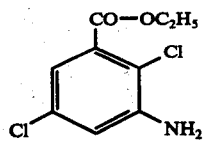

26.2 g (22 mmoles) of thionyl chloride were added dropwise to 300 ml of ethanol whilst stirring and cooling at between −5° C and 0° C and the mixture was then stirred for a further 30 minutes at 0° C. 40.8 g (20 mmoles) of finely powdered 2,5-dichloro-3-aminobenzoic acid which had been dried over phosphorus pentoxide was now introduced over the course of one minute, the cooling bath was then replaced by a heating bath, and the mixture was heated under reflux for 16 hours. The solvent was then completely evaporated off in vacuo and the residue was shaken with dilute sodium hydroxide solution [12 g (30 mmoles) of NaOH in 250 ml of water] and was extracted once with 300 ml of ether and twice with 100 ml of ether at a time. The combined organic phases were dried over magnesium sulfate and worked up in the usual manner. 46 g of a pale brown oil, which slowly crystallized at room temperature, remained. The solid was recrystallized from cyclohexane. 40 g (86% of theory) of 2,5-dichloro-3-amino-benzoic acid ethyl ester of melting point 63°–65° C were obtained.

EXAMPLE VI — Preparation of 2,5-dichloro-3-amino-benzoic acid N-methylamide

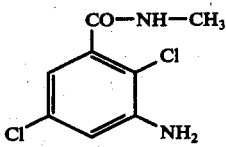

4.64 g (20 mmoles) of 2,5-dichloro-3-amino-benzoic acid ethyl ester, 40 ml of 30–40% strength methylamine solution and 0.5 ml of methanol were stirred for 2 hours at 40° C in a closed reaction vessel. The mixture was then evaporated to dryness in vacuo. The residue was shaken vigorously with 50 ml of water, filtered off, dried over phosphorus pentoxide and recrystallized from ethylene chloride. 2.9 g (66% of theory) of 2,5-chloro-3-aminobenzoic acid N-methylamide of melting point 165°–170° C were obtained.

The active compounds according to the invention influence plant growth and can therefore be used as defoliants, desiccants, agents for destroying broad-leaved plants, germination preventatives and, in particular, weed-killers. Weeds in the broadest sense are to be understood as all plants which grow in locations where they are undesired. Whether the compounds according to the invention act as total herbicides or selective herbicides depends essentially on the amount used.

The active compounds according to the invention can be used, for example, with the following plants:

Dicotyledon weeds (genera): mustard (Sinapis), cress (Lepidium), bed straw (Galium), chickweed (Stellaria), camomile (Matricaria), mayweed (Anthemis), gallant soldier (Galinsoga), goosefoot (Chenopodium), annual nettle (Urtica), groundsel (Senecio), pigweed (Amaranthus), purslane (Portulaca), cocklebur (Xanthium), bindweed (Convolvulus), morning glory (Ipomoea), knotweed (Polygonum), sesbania (Sesbania), ragweed (Ambrosia), spear thistle (Cirsium), common thistle (Carduus), sow thistle (Sonchus), nightshade (Solanum), field cress (Rorippa), toothcup (Rotala), false pimpernel (Lindernia), deadnettle (Lamium), speedwell (Veronica), mallow (Abutilon), emex (Emex), thornapple (Datura), violet (Viola), hemp nettle (Galeopsis), poppy (Papaver) and knapweed (Centaurea).

Dicotyledon cultures (genera): cotton (Gossypium), soya bean (Glycine), beet (Beta), carrot (Daucus), bean (Phaseolus), pea (Pisum), potato (Solanum), flax (Linum), morning glory (Ipomoea), broad bean (Vicia), tobacco (Nicotiana), tomato (Lycopersicon), groundnut (Arachis), cabbage (Brassica), lettuce (Lactuca), cucumber (Gucumis) and marrow (Cuburbita).

Monocotyledon weeds (genera): barnyard grass (Echisochloa), foxtail (Setaria), wild millet (Panicum), crabgrass (Digitaria), timothy (Phleum), bluegrass (Poa), fescue (Festuca), goosegrass (Eleusine), signalgrass (Brachiaria), ryegrass (Lolium), cheat (Bromus), oats (Avena), flatsedge (Cyperus), sorghum (Sorghum), quackgrass (Agropyron), Bermuda grass (Cynodon), Monocharia, fimbristylis, (Fimbristylis) arrowhead (Sagittaria), spikerush (Eleocharis), bulrush (Scirpus), paspalum (Paspalum), Ischaemum, gooseweed (Sphenoclea), crowfoot grass (Dactyloctenium), redtop (Agrostis), meadow foxtail (Alopercurus) and silky bent-grass (Apera).

Monocotyledon cultures (genera): rice (Oryza), maize (Zea), wheat (Triticum), barley (Hordeum), oats (Avena), rye (Secale), sorghum (Sorghum), millet (Panicum), sugar cane (Saccharum), pineapple (Ananas), asparagus (Asparagus) and onion (Allium).

However, the use of the active compounds according to the invention is in no way restricted to these genera but also covers other plants in the same way.

Depending on the concentration, the compounds can be used for the total combating of weeds, for example on industrial terrain and rail tracks, and on paths and open areas where there may or may not be trees growing. Equally, the compounds can be used for combating weeds in permanent cultures, for example forestry, horticultural tree nurseries, orchards, vineyards, citrus fruit orchards, nut plantations, banana plantations, coffee plantations, tea plantations, rubber plantations, palm oil plantations, cocoa plantations, soft fruit plantings and hopfields, and for the selective combating of weeds in annual cultures.

The active compounds according to the invention can, depending on the intended use, be combined with other herbicidally active compounds to boost their action and supplement their spectrum of action; it is possible to employ ready-to-use formulations of tank mixing. In particular, the active compounds mentioned below, and other representatives of the groups of active compound characterized by these active compounds, are suitable for this purpose.

2,3,6-Trichlorobenzoic acid and its salts, 2,3,5,6-tetrachlorobenzoic acid and its salts, 3-nitro-2,5-dichlorobenzoic acid and its salts, 3-amino-2,5-dichlorobenzoic acid and its salts, 2-methoxy-3,6-dichlorobenzoic acid and its salts, 2-methoxy-3,5,6-trichlorobenzoic acid and its salts, 2,6-dichloro-thiobenzamide, 2,6-dichlorobenzonitrile, 2,4-dichlorophenoxyacetic acid and its salts and esters, 2,4,5-trichlorophenoxyacetic acid and its salts and esters, (2-methyl-4-chlorophenoxy)-acetic acid and its salts and esters, 2-(2,4-dichlorophenoxy)-propionic acid, 2-(2-methyl-4-chlorophenoxy)-propionic acid and 2-(2,4,5-trichlorophenoxy)-propionic acid and their salts and esters, 4-(2,4-dichlorophenoxy)-butyric acid and its salts and esters, 4-(2-methyl-4-chlorophenoxy)-butyric acid and its salts and esters, 2,3,6-trichlorophenylacetic acid and its salts and 4-amino-3,5,6-trichloropicolinic acid.

Trichloroacetic acid and its salts, 2,2-dichloropropionic acid and its salts, 2-chloro-N,N-diallylacetic acid amide, dinitrocresol, dinitro-sec.-butylphenol and its salts.

3-Phenyl-1,1-dimethyl-urea, 3-(4'-chlorophenyl)-1,1-dimethyl-urea, 3(-(3',4'-dichlorophenyl)-1,1-dimethyl-urea, 3-(3',4'-dichlorophenyl)-1-n-butyl-1-methyl-urea, 3-(3',4'-dichlorophenyl)-1,1,3-trimethyl-urea, 3-(4'-chlorophenyl)-1-methoxy-1-methyl-urea, 3-(3'-trifluoromethyl-phenyl)-1,1-dimethyl-urea, 3-(3',4'-dichlorophenyl)-1-methoxy-1-methyl-urea, 3-(4'-bromophenyl)-1-methoxy-1-methyl-urea, 3-(3',4'-dichlorophenyl)-3-methoxy-1,1-dimethyl-urea, 3-(4'-chlorophenoxyphenyl)-1,1-dimethyl-urea, N'-cyclooctyl-N,N-dimethyl-urea, 3-(benzthiazol-2-yl)-1,3-dimethyl-urea and 3-(3-chloro-4-methylphenyl)-1,1-dimethyl-urea.

N,N-di-(n-propyl)-S-n-propyl-thiocarbamic acid ester, N-ethyl-N-(n-butyl)-S-n-propyl-thiocarbamic acid ester, N,N-di-(n-propyl)-S-ethyl-thiocarbamic acid ester, N-phenyl-O-isopropyl-carbamic acid ester, N-(m-chlorophenyl)-)-isopropylcarbamic acid ester, N-(3',4'-dichlorophenyl)-O-methylcarbamic acid ester, N-(m-chlorophenyl)-O-(4-chloro-butin-(2)-yl)-carbamic acid ester, N-(3'-methylphenyl)-o-(3-methoxycarbonylaminophenyl)-carbamic acid ester and N,N-diisopropylthiocarbamic acid 2,3,3-trichloroallyl ester.

3-Cyclohexyl-5,6-trimethylene-uracil, 5-bromo-3-sec.-butyl-6-methyl-uracil, 3,6-dioxo-1,2,3,6-tetrahydropyridazine and 4-amino-5-chloro-1-phenyl-pyridazone-(6).

2-Chloro-4-ethylamino-6-isopropylamino-s-triazine, 2-chloro-4,6-bis-(methoxypropylamino)-s-triazine, 2-methoxy-4,6-bis-(isopropylamino)-s-triazine, 2-diethylamino-4-isopropylacetamide-6-methoxy-s-triazine, 2-isopropylamino-4-methoxypropylamino-6-methylthio-s-triazine, 2-methylthio-4,6-bis-(isopropylamino)-s-triazine, 2-chlor-4,6-bis-(ethylamino)-s-triazine, 2-methylthio-4,6-bis-(ethylamino)-s-triazine, 2-methoxy-4-ethylamino-6-isopropylamino-s-triazine, 2-methylthio-4-ethylamino-6-isopropylamino-s-triazine, 2-methoxy-4,6-bis-(ethylamino)-s-triazine and 2-chloro-4,6-bis-(isopropylamino)-s-triazine.

N,N-Diethyl-2,4-dinitro-6-trifluoromethyl-1,3-phenylenediamine, N,N-di-n-propyl-2,6-dinitro-4-trifluoromethyl-aniline, 4'-nitro-2,4-dichloro-diphenyl ether, 3,4-dichlorophenyl-propionamide and 2',6'-diethyl-N-(methoxymethyl)-2-chloroacetanilide.

The active compounds according to the present invention can be converted into the usual formulations, such as solutions, emulsions, suspensions, powders, pastes and granulates. These may be produced in known manner, for example by mixing the active compounds with extenders, that is liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylene, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexane, or strongly polar solvents, such as dimethyl formamide, dimethyl sulfoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaoline, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin sulfite waste liquors and methyl cellulose.

The active compounds according to the invention can be present in the formulations as a mixture with other active compounds, such as fungicides, insecticides, acaricides and, as stated above, other herbicides.

The formulations in general contain from 0.1 to 95 per cent by weight of active compound, preferably from 0.5 to 90 per cent by weight.

The active compounds can be used as such, in the form of their formulations or in the use forms prepared therefrom, such as ready-to-use solutions, emulsions, suspensions, powders, pastes and granules. They may be used in the customary manner, for example by spraying, atomizing, dusting, scattering and watering.

They can be used both by the post-emergence process and by the pre-emergence process; where the active compounds are used as total herbicides, they are preferably used after emergence of the plants, whereas when they are used for the selective combating of weeds they are preferably used before emergence.

The amount of active compound employed can vary within fairly wide limits. It depends essentially on the nature of the desired effect. In general, the amounts used are from 0.1 to 25 kg/ha, preferably from 0.25 to 10 kg/ha.

The present invention also provides a herbicidal composition containing as active ingredient a compound of the present invention in admixture with a solid or liquefied gaseous diluent or carrier or in admixture with a liquid diluent or carrier containing a surface-active agent.

The present invention also provides a method of combating weeds which comprises applying to the weeds or a weed habitat a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier. It will be seen that the usual methods of providing a harvested crop may be improved by the present invention.

The herbicidal activity of the present compounds is illustrated by the following biotest Example.

EXAMPLE A

Pre-emergence test

Solvent: 5 parts by weight of acetone
Emulsifier: 1 part by weight of alkylaryl polyglycol ether.

To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After 3 weeks, the degree of damage to the plants was determined in % damage in comparison to the development of the untreated control. The figures denote:

0% = no effect (as in untreated control)
100% = total destruction

The active compounds, the amounts applied and the results can be seen from the table which follows:

Table A

| Active compound | Amount of active compound used, kg/ha | Echinochloa | Chenopodium | Stellaria | Matricaria | Avena fatua | Wheat | Maize |
|---|---|---|---|---|---|---|---|---|
| 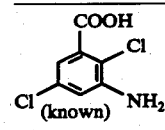 COOH, Cl, Cl, NH₂ (known) | 5<br>2.5 | 100<br>100 | 100<br>100 | 100<br>100 | 100<br>100 | 80<br>60 | 40<br>20 | 60<br>40 |
| 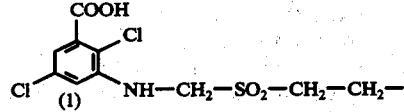 COOH, Cl, Cl, NH—CH₂—SO₂—CH₂—CH₂—Cl (1) | 5<br>2.5 | 100<br>100 | 100<br>100 | 100<br>100 | 100<br>100 | 60<br>60 | 0<br>0 | 40<br>40 |

Table A-continued

| Active compound | Pre-emergence test Amount of active compound used, kg/ha | Echinochloa | Chenopodium | Stellaria | Matricaria | Avena fatua | Wheat | Maize |
|---|---|---|---|---|---|---|---|---|
| 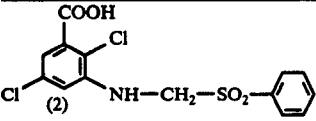 (2) | 5 2.5 | 100 100 | 100 100 | 100 100 | 100 100 | 40 40 | 0 0 | 20 0 |
| 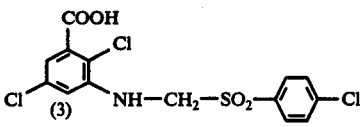 (3) | 5. 2.5 | 100 100 | 100 100 | 100 100 | 100 100 | 60 40 | 0 0 | 0 0 |
| 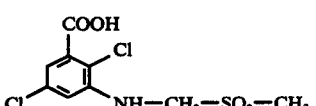 (5) | 5 2.5 | 100 100 | 100 100 | 100 100 | 100 100 | 80 60 | 0 0 | 40 20 |
| 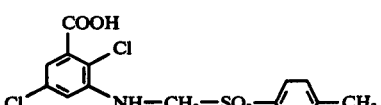 (4) | 5 2.5 | 100 100 | 100 100 | 100 100 | 100 100 | 80 60 | 0 0 | 40 20 |

It will be understood that the specification and examples are illustrative but not limitative of the present invention and that other embodiments within the spirit and scope of the invention will suggest themselves to those skilled in the art.

What is claimed is:

1. Method of combating undesirable vegetation which method comprises applying to a plant or its habitat a herbicidally effective amount of a benzoic acid compound of the formula

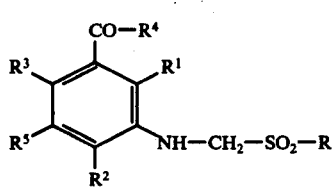

in which
R is alkyl or substituted alkyl of up to 6 carbon atoms, where the substituents are selected from halogen, or
R is aryl, and substituted aryl where the substituents are selected from halogen and alkyl of up to 4 carbon atoms,
$R^1$ is alkyl, alkoxy or alkylmercapto, of in each case up to 4 carbon atoms, or halogen,
$R^2$ is hydrogen,
$R^3$ is hydrogen or halogen, and
$R^4$ is hydroxyl;
$R^5$ is halogen or alkyl of up to 4 carbon atoms.

2. Method as claimed in claim 1 wherein said compound is selected from 2,5-dichloro-3-[(β-chloroethyl)-sulfonylmethylamino]-benzoic acid, 2,5-dichlor-3-phenylsulfonylmethylamino-benzoic acid, 2,5-dichloro-3-[(para-chlorophenyl)-sulfonylmethylamino]-benzoic acid, 2,5-dichloro-3-[(paratolyl-sulfonylmethylamino]-benzoic acid, and 2,5,6-trichloro-3-methylsulfonylmethylamino-benzoic acid.

3. Method as claimed in claim 1 wherein said compound is applied to an area of cultivation containing weeds in amount sufficient to substantially destroy the weeds without substantial injury to the crops.

4. Herbicidal composition comprising an agriculturally acceptable carrier and in effective amounts a benzoic acid compound as claimed in claim 1.

5. Benzoic acid compound of the formula

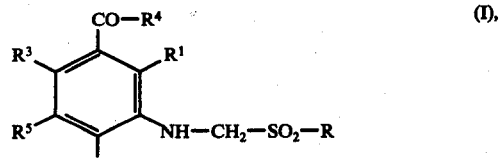

in which
R is alkyl or substituted alkyl of up to 6 carbon atoms, where the substituents are selected from halogen, or
R is aryl, and substituted aryl where the substituents are selected from halogen and alkyl of up to 4 carbon atoms,
$R^1$ is alkyl, alkoxy or alkylmercapto, of in each case up to 4 carbon atoms, or halogen,
$R^2$ is hydrogen,
$R^3$ is hydrogen or halogen, and
$R^4$ is hydroxyl,
$R^5$ is halogen or alkyl of up to 4 carbon atoms.

6. Benzoic acid compound as claimed in claim 5 wherein said compound is 2,5-dichloro-3-[(β-chloroethyl)-sulfonylmethylamino]-benzoic acid.

7. Benzoic acid compound as claimed in claim 5 wherein said compound is 2,5-dichloro-3-[phenyl-sulfonylmethylamino]-benzoic acid.

8. Benzoic acid compound as claimed in claim 5 wherein said compound is 2,5-dichloro-[(para-chlorophenyl)-sulfonylmethylamino]-benzoic acid.

9. Benzoic acid compound as claimed in claim 5 wherein said compound is 2,5-dichloro-3-[(para-tolyl)-sulfonylmethylamino]-benzoic acid.

10. Benzoic acid compound as claimed in claim 5 wherein said compound is 2,5,6-trichloro-3-methylsulfonylmethylamino-benzoic acid.

* * * * *